United States Patent
Moulton et al.

(10) Patent No.: US 12,268,547 B2
(45) Date of Patent: Apr. 8, 2025

(54) IMAGING METHOD FOR DIAGNOSING CARDIOVASCULAR DISEASE

(71) Applicant: Jubilant Draximage Inc., Montreal (CA)

(72) Inventors: Eric James Moulton, Montreal (CA); Robert A. DeKemp, Ottawa (CA); Indranil Nandi, Yardley, PA (US); Chad Roger Ronald Nicholas Hunter, Ottawa (CA)

(73) Assignee: Jubilant Draximage Inc. (CA)

( * ) Notice: Subject to any disclaimer, the term of this patent is extended or adjusted under 35 U.S.C. 154(b) by 119 days.

(21) Appl. No.: 18/242,131

(22) Filed: Sep. 5, 2023

(65) Prior Publication Data

US 2024/0074721 A1   Mar. 7, 2024

Related U.S. Application Data

(60) Provisional application No. 63/499,399, filed on May 1, 2023, provisional application No. 63/374,732, filed on Sep. 6, 2022.

(51) Int. Cl.
*A61B 6/00* (2024.01)
*A61B 6/03* (2006.01)
(Continued)

(52) U.S. Cl.
CPC ............ *A61B 6/5217* (2013.01); *A61B 6/037* (2013.01); *A61B 6/507* (2013.01); *A61B 6/5258* (2013.01);
(Continued)

(58) Field of Classification Search
CPC ....... A61B 6/5217; A61B 6/037; A61B 6/507; A61B 6/5258; A61B 6/503; G06T 5/70;
(Continued)

(56) References Cited

U.S. PATENT DOCUMENTS

| | | | | |
|---|---|---|---|---|
| 5,332,968 A | * | 7/1994 | Brown | G01R 33/563 324/309 |
| 12,144,669 B2 | * | 11/2024 | Min | A61B 6/503 |

(Continued)

*Primary Examiner* — Sanjay Cattungal
(74) *Attorney, Agent, or Firm* — William D. Hare; McNeely, Hare & War, LLP

(57) ABSTRACT

The present invention provides an image processing method to assess quantitative myocardial blood flow and/or myocardial flow reserve, comprising the steps of: (a) pre-processing of images comprises: (i) reconstructing dynamic cine 3D tomographic myocardial perfusion imaging (MPI) data, (ii) optionally, denoising to improve the quality of image, (iii) extracting blood input function from a region of interest (ROI) of the left ventricle blood cavity, (iv) estimating the distribution volume (DV), given by the ratio of uptake and washout rates ($K_1/k_2$) to stabilize and improve estimation of $K_1$, $k_2$ and total blood volume (TBV) and subsequent myocardial blood flow measures, and (v) data normalization by dividing by the maximum of the blood input function; (b) assessing the individual signals pre-processed in step (a) in order to generate $K_1$ and TBV parametric maps using artificial neural network;
(c) post-processing of $K_1$, $k_2$ and TBV parametric maps; and of rest and stress myocardial blood flow to estimate myocardial flow reserve (MFR) and/or coronary flow reserve (CFR).

19 Claims, 11 Drawing Sheets

(51) Int. Cl.
*A61B 6/50* (2024.01)
*G06T 5/70* (2024.01)
*G06T 7/00* (2017.01)
*G06T 11/00* (2006.01)
*G06V 10/25* (2022.01)
*G06V 10/82* (2022.01)

(52) U.S. Cl.
CPC .............. *G06T 5/70* (2024.01); *G06T 7/0012* (2013.01); *G06T 11/005* (2013.01); *G06V 10/25* (2022.01); *G06V 10/82* (2022.01); *G06T 2200/04* (2013.01); *G06T 2207/10104* (2013.01); *G06T 2207/20084* (2013.01); *G06T 2207/30104* (2013.01); *G06T 2211/441* (2023.08); *G06V 2201/03* (2022.01)

(58) Field of Classification Search
CPC . G06T 7/0012; G06T 11/005; G06T 2200/04; G06T 2207/10104; G06T 2207/20084; G06T 2207/30104; G06T 2211/441; G06T 2207/20081; G06T 7/0016; G06T 11/008; G06V 10/25; G06V 10/82; G06V 2201/03
See application file for complete search history.

(56) References Cited

U.S. PATENT DOCUMENTS

| | | | |
|---|---|---|---|
| 2005/0043614 A1* | 2/2005 | Huizenga | A61B 5/02007 600/427 |
| 2006/0064004 A1* | 3/2006 | Machida | G01R 33/4828 600/410 |
| 2008/0033291 A1* | 2/2008 | Rousso | A61B 5/416 600/436 |
| 2008/0042067 A1* | 2/2008 | Rousso | A61B 6/4258 250/363.04 |
| 2008/0119721 A1* | 5/2008 | Kimura | A61B 5/055 600/410 |
| 2008/0128626 A1* | 6/2008 | Rousso | A61B 6/4258 250/362 |
| 2008/0230705 A1* | 9/2008 | Rousso | A61B 5/4076 250/363.04 |
| 2013/0072790 A1* | 3/2013 | Ludwig | G06F 17/00 703/11 |
| 2014/0151563 A1* | 6/2014 | Rousso | G01T 1/1603 250/362 |
| 2014/0163368 A1* | 6/2014 | Rousso | A61B 6/4258 600/436 |
| 2014/0226890 A1* | 8/2014 | O'Brien | G01R 33/5608 382/131 |
| 2014/0303478 A1* | 10/2014 | Roche | G01R 33/5608 600/410 |
| 2018/0095152 A1* | 4/2018 | Triaire | A61B 5/055 |
| 2023/0380777 A1* | 11/2023 | DeKemp | A61M 5/168 |

* cited by examiner

IMAGING METHOD FOR DIAGNOSING CARDIOVASCULAR DISEASE

TECHNICAL FIELD

The present invention relates in general to nuclear imaging and medicine to assess quantitative myocardial blood flow and/or myocardial flow reserve.

BACKGROUND

Nuclear medicine employs radioactive material for therapy and diagnostic imaging. Different types of diagnostic imaging are there, which utilizes doses of radiopharmaceuticals. The doses of radiopharmaceuticals may be injected or infused into a patient prior to or during the diagnostic imaging procedure, wherein the radiopharmaceuticals can be absorbed by the cells or adhered to the cells of a target organ of the patient and emit radiation. The scanner or detector of the diagnostic imaging process can then detect the emitted radiation in order to generate an image of an organ. For an example, to image body tissue such as the heart muscle, a patient may be infused or injected with Rb-82 (i.e., Rubidium-82). The diagnostic imaging procedure can detect the radiation of Rb-82 and can get better images of myocardium and can diagnose the related problems.

Radioisotopes play a pivotal role in diagnosis and mitigation of various diseased conditions. For example, $^{60}$Co in treatment of cancer, $^{131}$I in treatment of hyperthyroidism, $^{14}$C in breath tests, $^{99m}$Tc and $^{82}$Rb as tracers in myocardial perfusion imaging.

Further, Rubidium-82 is produced in-situ by radioactive decay of Strontium-82. Rubidium elution systems utilize doses of rubidium-82 generated by elution within a radioisotope generator, and infuse or inject the radioactive solution into a patient.

Previously, preclinical studies in dogs showing that myocardial uptake of Rb-82 radionuclide was directly related to myocardial blood flow (MBF). Dynamic cine myocardial perfusion imaging (MPI) with radioisotopes can produce accurate prediction of myocardial blood flow (MBF) and myocardial flow reserve (MFR). Typically, MBF estimation begins with segmentation of the left ventricle (LV) myocardium followed by tracer kinetic modeling in a limited number of two-dimensional (2D) polar-map sectors or segments. However, two-dimensional (2D) polar-map segments have drawbacks. Few cardiac disorders related to flow in small regional flow defect can be visualized properly in two-dimensional (2D) polar-map. Therefore, there is an alternate method of myocardial perfusion imaging by visualizing three-dimensional (3D) parametric maps of MBF. But, there are some disadvantages in practicing of visualizing three-dimensional (3D) parametric maps of MBF. Further, in identifying small regional flow defects are not always visible. Additionally, generating the three-dimensional (3D) parametric maps is time consuming and is less stable. These disadvantages discourage the healthcare providers to adopt the use of 3D parametric maps of MBF for estimating myocardial blood flow. Therefore, there is a need of an alternative approach to generate more stable three-dimensional (3D) parametric maps in lesser time to estimate the myocardial blood blow and flow reserve.

Rb-82 PET imaging was performed using a single fixed dose for all patients, due in part to limitations of early-generation tracer delivery systems. This undesirable effect of old PET imaging system can be mitigated to some extent by using the advanced and latest generation Rb-82 elution system. The present inventors observed that by using the 3D parametric imaging of myocardial perfusion with Rb-82 PET can accurately estimate and/or predict myocardial blood flow (MBF) and/or myocardial flow reserve (MFR).

SUMMARY

The present invention aims to provide an image processing method to assess quantitative myocardial blood flow (MBF) and/or myocardial flow reserve (MFR).

The object of the present invention is to provide an alternate method to use 3D voxel-wise parametric imaging data to estimate and/or predict quantitative myocardial blood flow (MBF) and/or myocardial flow reserve (MFR), which may better highlight small regional flow defects. More precisely, the inventors of the present invention estimate the myocardial blood flow (MBF) and/or myocardial flow reserve (MFR), wherein the image series fit to a one-tissue-compartment model yielding voxel-wise parametric maps comparing the projected data onto a two-dimensional (2D) polar map of the left ventricle (LV). The present invention, therefore, has an advantage of producing regional flow and reserve values, which may better highlight small regional flow defects and are independent of LV polar-map segmentation.

The object of the present invention is to provide an image processing method to assess quantitative myocardial blood flow and/or myocardial flow reserve, wherein the image reconstruction algorithms have been developed to improve the quality of images and using the AI algorithm to enhance the image reconstruction quality, which intended to do the image processing faster and reduce the doses of nuclear medicine up to 10 times during the myocardial perfusion imaging (MPI).

The object of the present invention for AI models can generate blood flow parametric maps with high accuracy and in a timeframe acceptable for clinical use and thus may enable future clinical implementation.

The object of the present invention is to provide an image processing method to assess quantitative myocardial blood flow and/or myocardial flow reserve, wherein 3D parametric images of MBF generated by present invention also recommend the calcium scoring.

In an embodiment of the present invention, an image processing method to assess quantitative myocardial blood flow and myocardial flow reserve, comprising the steps of:
a. pre-processing of images comprises:
   (i) reconstructing dynamic cine 3D tomographic myocardial perfusion imaging (MPI) data,
   (ii) isolating value at voxel (i,j,k) for each time point $t_j$ where i is from 1 to N, (iii) optionally, denoising to improve the quality of image,
   (iv) extracting blood input function from a region of interest (ROI) of the left ventricle blood cavity or other arterial blood region of region of interest (ROI),
   (v) estimating the distribution volume (DV), given by the ratio of uptake and washout rates ($K_1/k_2$) to stabilize and improve estimation of $K_1$ and total blood volume (TBV) and subsequent myocardial blood flow measures, and
   (vi) data normalization by dividing by the maximum of the blood input function;
b. assessing the individual signals pre-processed in step (a) in order to generate $K_1$ and TBV parametric maps using artificial neural network;

c. post-processing of $K_1$ and TBV parametric maps; and of rest and stress myocardial blood flow to estimate myocardial flow reserve (MFR) and/or coronary flow reserve (CFR).

In an embodiment of the present invention includes the image processing method to assess quantitative myocardial blood flow and myocardial flow reserve, wherein the image reconstruction of arrays is a dynamic cine series comprising the 3D tomographic voxel (i,j,k) from PET reconstruction for the number of time steps, $t_i$, where i is from 1 to N.

Yet in an embodiment of the present invention includes the image processing method to assess quantitative myocardial blood flow and myocardial flow reserve, wherein the input signal enters a multi-layer perceptron (MLP), an artificial neural network and/or convolutional neural network (CNN) and/or long short term memory (LSTM) network to simultaneously predict uptake rate ($K_1$), washout rate ($k_2$) and total blood volume (TBV).

In another embodiment of the present invention includes the image processing method to assess quantitative myocardial blood flow and/or myocardial flow reserve, wherein the imaging agent or radionuclide is administered by automated generation and infusion system and/or intravenous administration of radiopharmaceuticals produced by fission, neutron activation, cyclotron, generator and/or combinations thereof.

Yet in embodiment of the present invention includes an image processing method to assess quantitative myocardial blood flow and myocardial flow reserve, comprising the steps of:
a. pre-processing of images comprises:
   (i) reconstructing dynamic cine 3D tomographic myocardial perfusion imaging (MPI) data,
   (ii) isolating value at voxel (i,j,k) for each time point $t_i$ where i is from 1 to N, (iii) optionally, denoising to improve the quality of image,
   (iv) extracting blood input function from a region of interest (ROI) of the left ventricle blood cavity or other arterial blood region of interest (ROI),
   (v) estimating the distribution volume (DV), given by the ratio of uptake and washout rates ($K_1/k_2$) to stabilize and improve estimation of $K_1$, $k_2$ and total blood volume (TBV) and subsequent myocardial blood flow measures, and
   (vi) data normalization by dividing by the maximum of the blood input function,
b. applying the time series at voxel (i,j,k) and blood input function to artificial intelligence network simultaneously to predict uptake $K_1$, $k_2$ and TBV,
c. post-processing of $K_1$, $k_2$ and TBV parametric maps comprises:
   (i) partial volume correction,
   (ii) extraction fraction to estimate myocardial blood flow (MBF) at rest and stress; and
d. post-processing of rest and stress myocardial blood flow to estimate myocardial flow reserve (MFR) and/or coronary flow reserve (CFR);
wherein the artificial neural networks are selected from the group consisting of, multi-layer perceptron (MLP), artificial neural network (ANN), convolutional neural network (CNN), recurrent neural network (RNN), long short-term memory recurrent neural network (LSTM-RNN), gated recurrent unit (GRU) network, Generative adversarial networks (GANs), deep machine learning and/or combinations thereof.

BRIEF SUMMARY OF DRAWINGS

Further features and advantages of the present invention will become apparent from the following detailed description, taken in combination with the appended drawings, in which.

DETAILED DESCRIPTION

Figure 1:
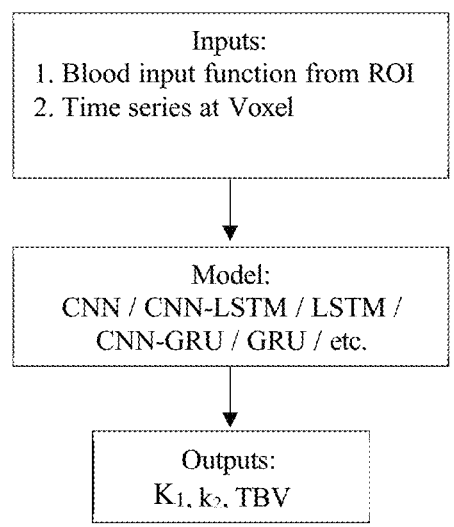
FIG. 1 depicts the flow diagram, wherein the model takes blood input function, and the time series at voxel for output $K_1$, $k_2$ and TBV (total blood volume).

There is currently a need to improve radioisotope imaging procedure to estimate and/or predict small regional dysfunction or disorders related to the myocardial blood flow (MBF) and/or myocardial flow reserve (MFR), wherein the image series fit to a one-tissue-compartment model yielding voxel-wise parametric maps comparing the projected data onto a two-dimensional (2D) polar map of the organ of interest such as left ventricle (LV) myocardium. The inventors of the present invention surprisingly found the advantage of producing regional flow and reserve values, which may better highlight small regional flow defect and are independent of LV polar-map segmentation. The inventors of the present invention found that by using an alternative 3D parametric imaging method of myocardial perfusion with radioisotopes can accurately estimate and/or predict the myocardial blood flow (MBF) and/or myocardial flow reserve (MFR). The present invention can be more readily understood by reading the following detailed description of the invention and included embodiments.

As used herein, the term "imaging" refers to techniques and processes used to create images of various parts of the human body for diagnostic and treatment purposes within digital health. X-ray radiography, Fluoroscopy, Magnetic resonance imaging (MRI), Computed Tomography (CT), Medical Ultrasonography or Ultrasound Endoscopy Elastography, Tactile imaging, Thermography Medical photography, and nuclear medicine functional imaging techniques e.g. Positron Emission Tomography (PET), Dynamic Positron Emission Tomography or Single-photon Emission Computed Tomography (SPECT). Imaging seeks to reveal internal structures of the body, as well as to diagnose and treat disease.

As used herein, the term "Positron Emission Tomography (PET)" refers to a functional imaging technique that uses radioactive substances known as radiotracers or radionuclides to visualize and measure changes in metabolic processes, and in other physiological activities including blood flow, regional chemical composition, and absorption. Different tracers can be used for various imaging purposes, depending on the target process within the body commonly used radionuclide isotopes for PET imaging include Rb-82 (Rubidium-82), Water O-15 (Oxygen-15), F-18 (Fluorine-18), Ga-68 (Gallium-68), Cu-61 (Copper-61), C-11 (Carbon-11), N-13 (Ammonia-13), Co-55 (Cobalt-55), Zr-89 (Zirconium-89), Cu-62, Cu-64, I-124, Tc-99m (Technetium), Tl-201 (Thallium-201), and FDG (Fluorodeoxyglucose). The preferred radionuclide comprises Rb-82 having a half-life of 75 seconds.

As used herein, the term "SPECT" refers to a Single-photon emission computed tomography is a nuclear medicine tomographic imaging technique using gamma rays and provide true 3D information. This information is typically presented as cross-sectional slices through the patient, but can be freely reformatted or manipulated as required. The technique requires delivery of a gamma-emitting radioisotope (a radionuclide) into the patient, normally through injection into the bloodstream. A marker radioisotope is generally attached to a specific ligand to create a radioligand, whose properties bind it to certain types of tissues. This allows the combination of ligand and radiopharmaceutical to be carried and bound to a region of interest in the body, where the ligand concentration is assessed by a gamma camera. SPECT agents include $^{99m}$Tc technetium-99m ($^{99m}$Tc)-sestamibi, and $^{99m}$Tc-tetrofosmin), In-111, Ga-67, Ga-68, Tl-201 (Thallium-201).

As used herein, the term "diagnosis" refers to a process of identifying a disease, condition, or injury from its signs and symptoms. A health history, physical exam, and tests, such as blood tests, imaging, scanning, and biopsies can be used to help make a diagnosis.

As used herein, the term "assessment" refers to a qualitative and/or quantitative assessment of the blood perfusion in a body part or region of interest (ROI).

As used herein, the term "stress agent" refers to agents used to generate stress in a patient or a subject during imaging procedure. The stress agents according to the present invention are selected from vasodilator agent for example adenosine, adenosine triphosphate and its mimetic, A2A adenosine receptor agonist for example regadenoson or adenosine reuptake inhibitor dipyridamole, other pharmacological agent to increase blood flow to the heart, like catecholamines (for example dobutamine, acetyl-choline, papaverine, ergovine, etc.) or other external stimuli to increase blood flow to the heart such as cold-press, mental stress or physical exercise.

As used herein, the term "automated infusion system" or "radionuclide generation" and/or "infusion system" or "Rb-82 elution system" refers to system for generation and/or infusion of a radionuclide or radiotracer and administration into a subject. The automated infusion system comprises radioisotope generator, dose calibrator, computer, controller, display device, activity detector, cabinet, cart, waste bottle, sensors, shielding assembly, alarms or alerts mechanism, tubing, source vial, diluent or eluant, valves. The automated infusion system can be communicatively or electronically coupled to imaging system.

As used herein, the term "dose" refers to the dose of radionuclide required to perform imaging in a subject. The dose of a radionuclide to be administered into the subject ranges from 0.01 MBq to 10,000 MBq.

As used herein, the term "coronary artery disease" or "cardiovascular disease" refers to a disease of major blood vessels. Cholesterol-containing deposits (plaques) in coronary arteries and inflammation are causes of coronary artery disease. The coronary arteries supply blood, oxygen and nutrients to your heart. A buildup of plaque can narrow these arteries, decreasing blood flow to your heart. Eventually, the reduced blood flow may cause chest pain (angina), shortness of breath, or other coronary artery disease signs and symptoms. Significant blockage of the arteries can cause a heart attack. It can be diagnosed by imaging of the myocardium and/or myocardial blood flow (MBF) under rest or pharmacologic stress conditions to evaluate regional myocardial perfusion.

As used herein, the term "myocardial blood flow (MBF)" can be defined as the volume of blood transiting through tissue at a certain rate. MFR constitutes the ratio of MBF during maximal coronary vasodilatation to resting MBF and is therefore impacted by both rest and stress flow. MFR represents the relative reserve of the coronary circulation.

As used herein, the term "radionuclide" or "radioisotope" refers to an unstable form of a chemical element that releases radiation as it breaks down and becomes more stable. Radionuclides can occur in nature or can be generated in a laboratory. In medicine, they are used in imaging tests and/or in treatment.

As used herein, the term "Sr/Rb elution system" or "$^{82}$Sr/$^{82}$Rb elution system" refers to infusion system meant for generating a solution containing Rb-82, measuring the radioactivity in the solution, and infusing the solution into a subject in order to perform various studies on the subject region of interest.

As used herein, the term "image counts" refers to number of radioisotope disintegrations acquired per unit time by the PET scanner.

As used herein, the term "generator" or "radioisotope generator" refers to a hollow column inside a radio-shielded container. The column is filled with an ion exchange resin and radioisotope loaded onto the resin. Radionuclide generator according to the present invention is selected from $^{99}$Mo/$^{99m}$Tc, $^{90}$Sr/$^{90}$Y, $^{82}$Sr/$^{82}$Rb, $^{188}$W/$^{188}$Re, $^{68}$Ge/$^{68}$Ga $^{42}$Ar/$^{42}$K, $^{44}$Ti/$^{44}$Sc, $^{52}$Fe/$^{52m}$Mn, $^{72}$Se/$^{72}$As, $^{83}$Rb/$^{83m}$Kr $^{103}$Pd/$^{103m}$Rh, $^{109}$Cd/$^{109m}$Ag, $^{113}$Sn/$^{113m}$In, $^{118}$Te/$^{118}$Sb, $^{132}$Te/$^{132}$I, $^{137}$Cs/$^{137m}$Ba $^{140}$Ba/$^{140}$La, $^{134}$Ce/$^{134}$La, $^{144}$Ce/$^{144}$Pr $^{140}$Nd/$^{140}$Pr, $^{166}$Dy/$^{166}$Ho, $^{167}$Tm/$^{167m}$Er, $^{172}$Hf/$^{172}$Lu, $^{178}$W/$^{178}$Ta, $^{191}$Os/$^{191m}$Ir $^{194}$Os/$^{194}$Ir, $^{226}$Ra/$^{222}$Rn and $^{225}$Ac/$^{213}$Bi, $^{64}$Zn/$^{61}$Cu.

As used herein, the term "eluant" refers to the liquid or the fluid used for selectively leaching out the daughter radioisotopes from the generator column.

As used herein, the term "eluate" refers to the radioactive eluant after acquisition of daughter radioisotope from the generator column.

As used herein, the term "controller" refers to a computer or a part thereof programmed to perform certain calculations, execute instructions, and control various activities of an elution system based on user input or automatically.

As used herein, the term "activity detector" refers to a component that is used to determine the amount of radioactivity present in eluate from a generator, e.g., prior to the administration of the eluate to the patient.

As used herein, the term "Convolutional Neural Network (CNN)" refers to a system resembles feed forward neural systems. It is a type of artificial neural network used in time series and image and processing that is specifically designed to process pixel data. In deep learning, a convolutional neural network (CNN/ConvNet) is a class of deep neural networks, most commonly applied to analyze time series as well as natural or medical images. The blood input function is extracted from a region of interest (ROI) using manual or automatic procedures. The mean signal within the ROI is extracted at every time point creating a 1D signal blood input function.

As used herein, the term "Multi-layer perceptron (MLP)" refer to the Multilayer Perceptron is an example of an artificial neural network that is used extensively for the solution of a number of different problems, including pattern recognition and interpolation.

As used herein, the term "Recurrent neural network (RNN)" refers to a special type of an artificial neural network adapted to work for time series data or data that involves sequences. Ordinary feed forward neural networks are only meant for data points, which are independent of each other. RNN method can be long short-term memory (LSTM) or Gated Recurrent Unit (GRU) network. RNNs can work in conjunction with CNNs to form networks, such as the CNN-LSTM.

As used herein, the term "Gated Recurrent Unit (GRU)" refers to a type of Recurrent Neural Network (RNN) and uses less memory. It is a part of a specific model of recurrent neural network that intends to use connections through a sequence of nodes to perform machine learning tasks associated with memory and clustering. It has a gating mechanism in recurrent neural networks.

As used herein, the term "voxel" refers a value on a regular grid in three-dimensional space in three-dimensional (3D) computer graphics. Voxel is short for volume pixel, the smallest distinguishable cube-shaped part of a 3D image. Voxelization is the process of adding depth to an image using a set of cross-sectional images known as a volumetric dataset. These cross-sectional images (or slices) are made up of pixels. Pulling pixels and slices together, a three-dimensional (3D) partition of the image space into volume elements (voxels) forming a 3D scalar field.

As used herein, the term "Tissue Response Function (TRF)" refers as a tracer kinetic modelling, which is used to estimate physiological parameters such as myocardial blood flow (MBF) by mapping or transforming the shape of the "arterial input function (AIF)" to the shape of TRF.

As used herein, the term "blood input function" refers commonly known as arterial input function (AIF), which is defined as the concentration of the tracer in an artery measured over time by placing a region of interest.

In an embodiment of the present invention includes an image processing method to assess quantitative myocardial blood flow and myocardial flow reserve, comprising the steps of:
  a. pre-processing of images comprises:
    (i) reconstructing dynamic cine 3D tomographic myocardial perfusion imaging (MPI) data,
    (ii) isolating value at voxel (i,j,k) for each time point $t_i$ where i is from 1 to N,
    (iii) optionally, denoising to improve the quality of image,
    (iv) extracting blood input function from a region of interest (ROI) of the left ventricle blood cavity or other arterial blood region of interest (ROI),
    (v) estimating the distribution volume (DV), given by the ratio of uptake and washout rates ($K_1/k_2$) to stabilize and improve estimation of $K_1$, $k_2$ and total blood volume (TBV) and subsequent myocardial blood flow measures, and
    (vi) data normalization by dividing by the maximum of the blood input function,
  b. assessing the individual signals pre-processed in step (a) in order to generate $K_1$ and TBV parametric maps using artificial neural network;
  c. post-processing of $K_1$, $k_2$ ... $K_n$, $X^2$, $R^2$, distribution volume (DV) and TBV parametric maps, and of rest and stress myocardial blood flow to estimate myocardial flow reserve (MFR) and/or coronary flow reserve (CFR).

In an embodiment of the present invention includes the image processing method to assess quantitative myocardial blood flow and myocardial flow reserve, wherein the image reconstruction of arrays is a dynamic series comprising the 3D tomographic voxel (i,j,k) from PET reconstruction for the number of time steps, $t_i$, where i is from 1 to N.

In another embodiment of the present invention includes the image processing method to assess quantitative myocardial blood flow and myocardial flow reserve, wherein a region of interest (ROI) can be manual and/or automatic procedures.

Yet in an embodiment of the present invention includes the image processing method to assess quantitative myocardial blood flow and myocardial flow reserve, wherein the data normalization by dividing by the maximum of the blood input function.

In an embodiment of the present invention includes the image processing method to assess quantitative myocardial blood flow and myocardial flow reserve, wherein the data normalization for blood input function with the value is from 0 to 1.

In another embodiment of the present invention includes the image processing method to assess quantitative myocardial blood flow and myocardial flow reserve, wherein the input signal enters a multi-layer perceptron and/or an artificial neural network and/or generative adversarial network (GANs) and/or convolutional neural network (CNN) and/or long short term memory (LSTM) network to simultaneously predict uptake rate ($K_1$), washout rate ($k_2$), distributed volume (DV), and total blood volume (TBV).

Yet in an embodiment of the present invention includes the image processing method to assess quantitative myocardial blood flow and myocardial flow reserve, wherein the images produced regional flow and reserve values to highlight small regional flow defects.

In an embodiment of the present invention includes the image processing method to assess quantitative myocardial blood flow and myocardial flow reserve, wherein the artificial neural networks are selected from the group consisting of, multi-layer perceptron (MLP), artificial neural network (ANN), convolutional neural network (CNN), recurrent neural network (RNN), long short-term memory recurrent neural network (LSTM-RNN), gated recurrent unit (GRU) network, deep machine learning and/or combinations thereof.

In another embodiment of the present invention includes the image processing method to assess quantitative myocardial blood flow and myocardial flow reserve, wherein to estimate distribution volume (DV) artificial neural network enter in multiple layers and wherein the multiple layers can be selected from the group consisting of the initial layer of the network, at an intermediate layer, at the penultimate layer, or combinations thereof.

In an embodiment of the present invention includes the image processing method to assess quantitative myocardial blood flow and myocardial flow reserve, wherein the model predicts a $k_2$ (washout rate) value.

Yet in an embodiment of the present invention includes the image processing method to assess quantitative myocardial blood flow and myocardial flow reserve, wherein anisotropic diffusion filtering is with Gaussian filter.

In an embodiment of the present invention includes the image processing method to assess quantitative myocardial blood flow and myocardial flow reserve, wherein estimating $K_1$, $k_2$ and total blood volume (TBV) by performing on a voxel-wise basis using 1D signal CNN-LSTM to produce more accurate myocardial blood flow (MBF) estimations.

In another embodiment of the present invention includes the image processing method to assess quantitative myocardial blood flow and myocardial flow reserve, wherein the images are characterized by administering Rb-82, O-15, N-13, F-18, Cu-62, Tc-99m, Tl-201, and/or combinations thereof.

In an embodiment of the present invention includes the image processing method to assess quantitative myocardial blood flow and myocardial flow reserve, wherein the images are characterized by administering Rb-82 in rest and stress PET perfusion imaging to highlights small regional flow defects.

Yet in an embodiment of the present invention includes the image processing method to assess quantitative myocardial blood flow and myocardial flow reserve, wherein the imaging agent or radionuclide is administered by automated generation and infusion system and/or intravenous administration of radiopharmaceuticals produced by fission, neutron activation, cyclotron and/or generator.

In an embodiment of the present invention includes the image processing method to assess quantitative myocardial blood flow and myocardial flow reserve, wherein automated radioisotope generation and infusion system comprises Rb-82 elution system.

In another embodiment of the present invention includes the image processing method to assess quantitative myocardial blood flow and myocardial flow reserve, wherein the images obtained fit to one-tissue-compartment model or multi-tissue compartment model by predicting the value of the ratio of myocardial blood flow stress and myocardial blood flow rest to determine myocardial flow reserve and/or coronary flow reserve and wherein performing an assessment of the obtained images to diagnose disease state using multi-layer perceptron (MLP), artificial neural network (ANN), convolutional neural network (CNN), recurrent neural network (RNN), long short-term memory recurrent neural network (LSTM-RNN), gated recurrent unit (GRU) network, deep machine learning, deep neural network, artificial neural network and/or combinations thereof.

Yet in an embodiment of the present invention includes the image processing method to assess quantitative myocardial blood flow and myocardial flow reserve, wherein the imaging comprises positron emission tomography (PET) imaging, dynamic positron emission tomography, single-photon emission computerized tomography (SPECT), magnetic resonance imaging (MRI), computed tomography (CT), and/or combinations thereof.

In an embodiment of the present invention includes an image processing method to assess quantitative myocardial blood flow and myocardial flow reserve, comprising the steps of:
a. pre-processing of images comprises:
   (i) reconstructing dynamic cine 3D tomographic myocardial perfusion imaging (MPI) data
   (ii) isolating value at voxel (i,j,k) for each time point $t_i$ where i is from 1 to N,
   (iii) optionally, denoising to improve the quality of image,
   (iv) (extracting blood input function from a region of interest (ROI) of the left ventricle blood cavity or other arterial blood region of interest,
   (v) estimating the distribution volume (DV), given by the ratio of uptake and washout rates ($K_1/k_2$) to stabilize and improve estimation of $K_1$, $k_2$ and total blood volume (TBV) and subsequent myocardial blood flow measures, and
   (vi) data normalization by dividing by the maximum of the blood input function;
b. applying the time series at voxel (i,j,k) and blood input function to artificial intelligence network simultaneously to predict uptake K1, k2 and TBV,
c. post-processing of K1, k2 and TBV parametric maps comprises:
   (i) partial volume correction,
   (ii) extraction fraction to estimate myocardial blood flow (MBF) at rest and stress; and
d. post-processing of rest and stress myocardial blood flow to estimate myocardial flow reserve (MFR) and/or coronary flow reserve (CFR);

Yet in another embodiment of the present invention includes an image processing method to assess quantitative myocardial blood flow and myocardial flow reserve, comprising the steps of:
a. pre-processing of images comprises:
   (i) reconstructing dynamic cine 3D tomographic myocardial perfusion imaging (MPI) data,
   (ii) isolating value at voxel (i,j,k) for each time point $t_i$ where i is from 1 to N,
   (iii) optionally, denoising to improve the quality of image,
   (iv) extracting blood input function from a region of interest (ROI) of the left ventricle blood and other arterial blood region of interest,
   (v) estimating the distribution volume (DV), given by the ratio of uptake and washout rates ($K_1/k_2$) to stabilize and improve estimation of $K_1$, $k_2$ and total blood volume (TBV) and subsequent myocardial blood flow measures, and
   (vi) data normalization by dividing by the maximum of the blood input function;
b. applying the time series at voxel (i,j,k) and blood input function to artificial intelligence network simultaneously to predict uptake $K_1$, $k_2$ and TBV,
c. post-processing of $K_1$, $k_2$ and TBV parametric maps comprises:
   (i) partial volume correction,
   (ii) extraction fraction to estimate myocardial blood flow (MBF) at rest and stress; and
d. post-processing of rest and stress myocardial blood flow to estimate myocardial flow reserve (MFR) and/or coronary flow reserve (CFR);
wherein the artificial neural networks are selected from the group consisting of, multi-layer perceptron (MLP), artificial neural network (ANN), convolutional neural network (CNN), recurrent neural network (RNN), long short-term memory recurrent neural network (LSTM-RNN), gated recurrent unit (GRU) network, Generative adversarial networks (GANs), deep machine learning and/or combinations thereof.

Yet in another embodiment of the present invention includes an image processing method to assess quantitative myocardial blood flow and myocardial flow reserve, comprising the steps of:
a. pre-processing of images comprises:
   (i) reconstructing dynamic cine 3D tomographic myocardial perfusion imaging (MPI) data,
   (ii) isolating value at voxel (i,j,k) for each time point $t_i$ where i is from 1 to N, (iii) optionally, denoising to improve the quality of image,
   (iv) extracting blood input function from a region of interest (ROI) of the left ventricle blood cavity or other arterial blood region of interest (ROI),
   (v) estimating the distribution volume (DV), given by the ratio of uptake and washout rates ($K_1/k_2$) to stabilize and improve estimation of $K_1$, $k_2$ and total blood volume (TBV) and subsequent myocardial blood flow measures, and
   (vi) data normalization by dividing by the maximum of the blood input function;

b. applying the time series at voxel (i,j,k) and blood input function to artificial intelligence network simultaneously to predict uptake $K_1$ and TBV, wherein the average $R^2$ values are in between 0.9 to 1:
c. post-processing of $K_1$ and TBV parametric maps comprises:
  (i) partial volume correction,
  (ii) extraction fraction to estimate myocardial blood flow (MBF) at rest and stress; and
d. post-processing of rest and stress myocardial blood flow to estimate myocardial flow reserve (MFR) map and/or coronary flow reserve (CFR) map;
wherein the artificial neural networks are selected from the group consisting of, multi-layer perceptron (MLP), artificial neural network (ANN), convolutional neural network (CNN) and/or 1D convolutional neural network (1D-CNN), recurrent neural network (RNN), long short-term memory recurrent neural network (LSTM-RNN), gated recurrent unit (GRU) network, generative adversarial networks (GANs), deep machine learning and/or combinations thereof.

FIG. 1 illustrating the flow diagram, wherein the model takes blood input function, the timeseries at voxel for output $K_1$, $k_2$ and TBV (total blood volume).

Figure 2:
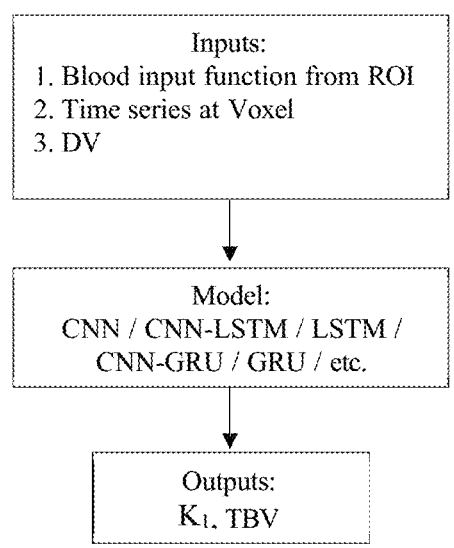
FIG. 2 Depicts the flow diagram, wherein the model takes blood input function, the time series at voxel, and distribution volume (DV) for output $K_1$ and TBV (total blood volume).

The flow diagram of FIG. 2 illustrating the model that takes blood input function, the timeseries at voxel, distribution volume (DV) for output $K_1$ and TBV (total blood volume).

Figure 3:
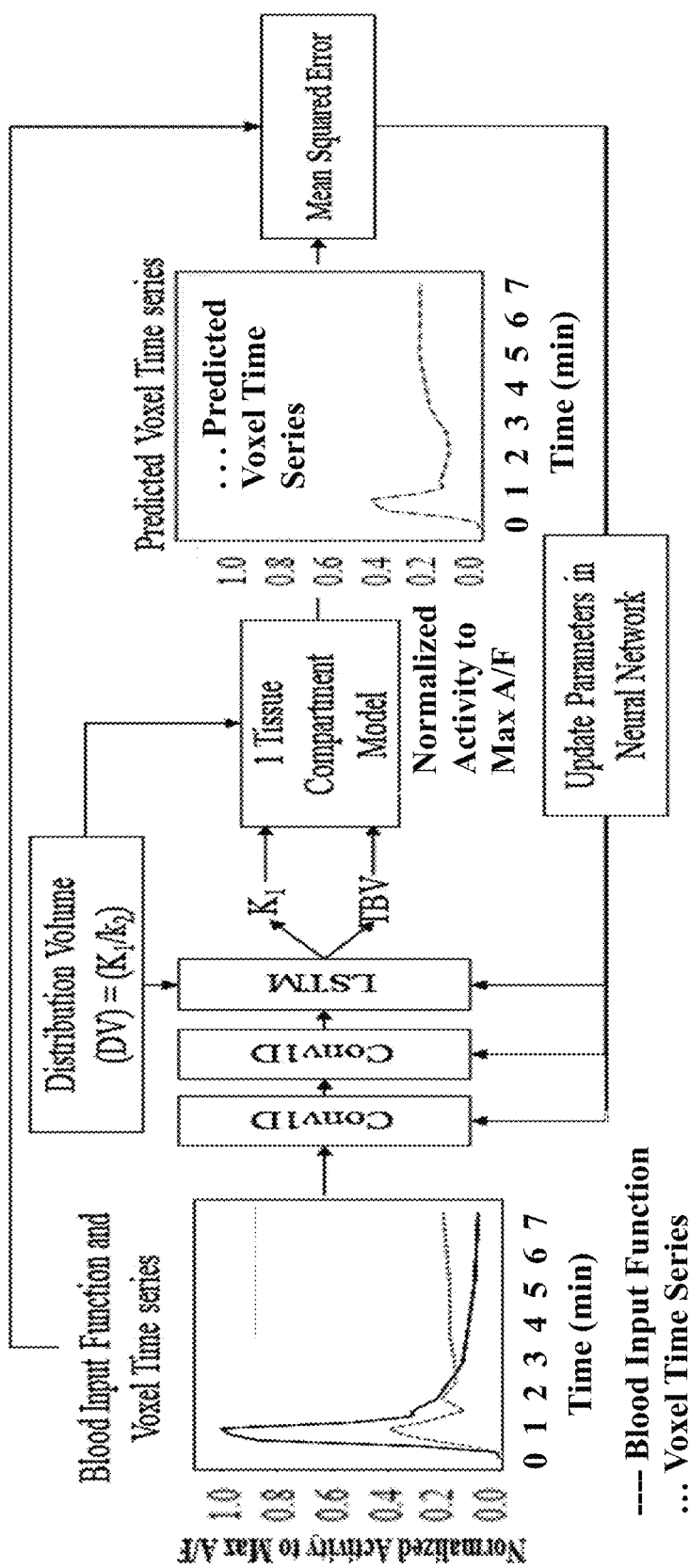
FIG. 3 depicts the flow diagram for model training.
Figure 4:
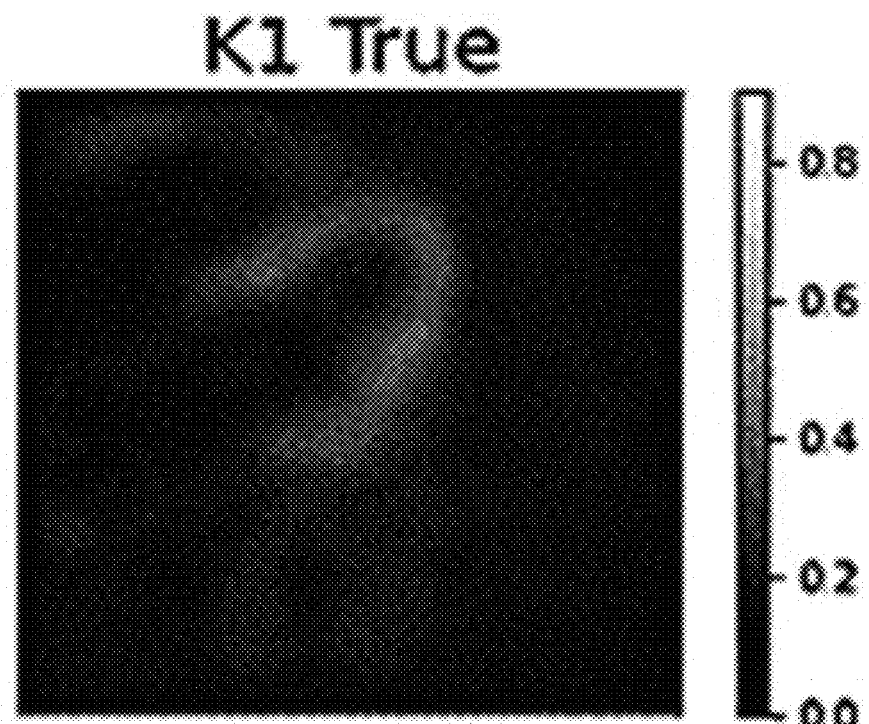
FIGS. 4-19 represent ground truth vs AI-generated parametric maps.
Figure 5:
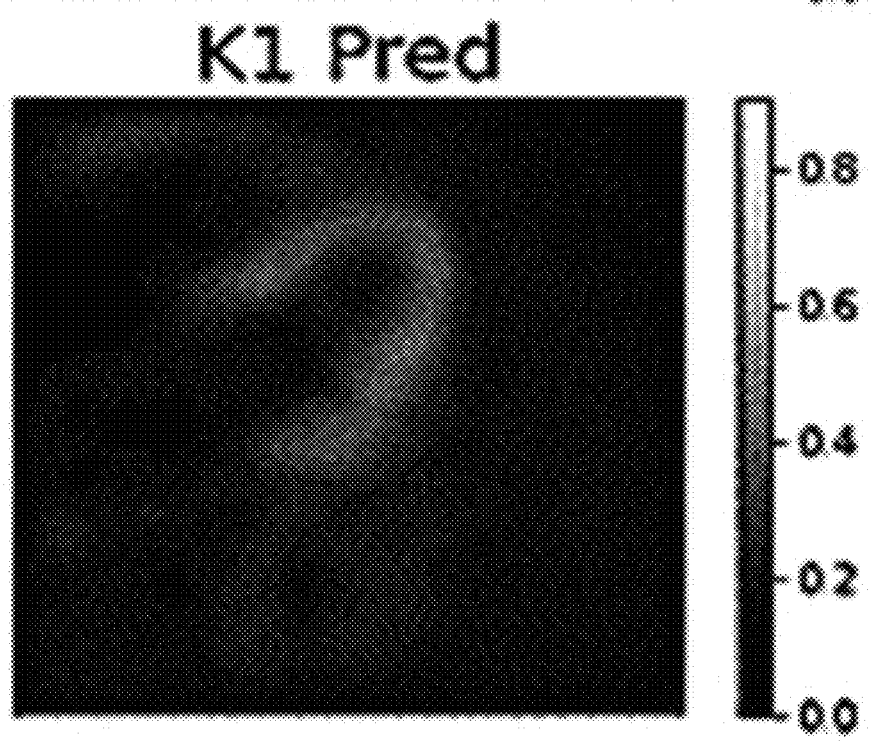
Figure 6:
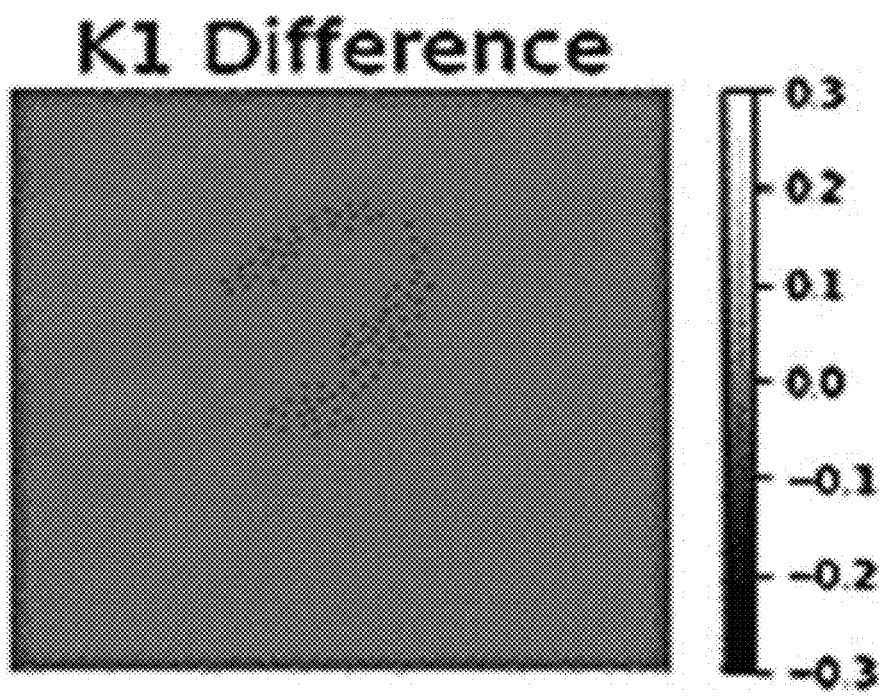

FIG. 3 illustrating the flow diagram for model training, wherein the model takes blood input function, time series at voxel, and distribution volume (DV) for output $K_1$ and TBV (total blood volume). $K_1$, TBV, and DV are inputs to the one tissue compartment model which yields a predicted voxel time series. The mean squared error between the predicted and input voxel time series is computed and feedback to the model to update model parameters.

Figure 7:
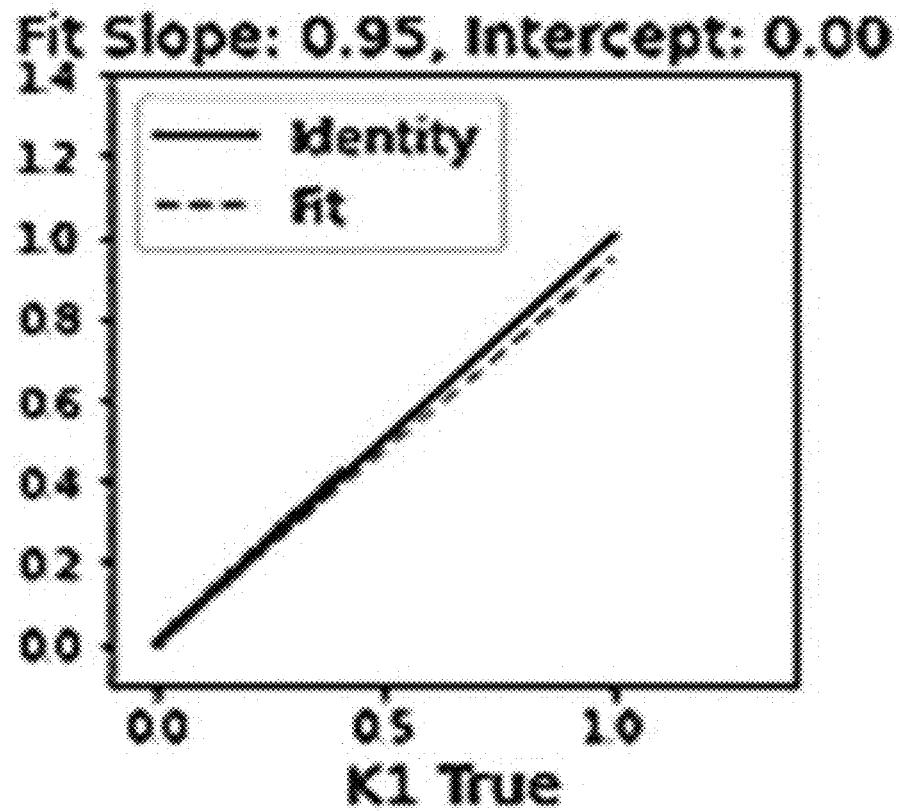
Figure 8:
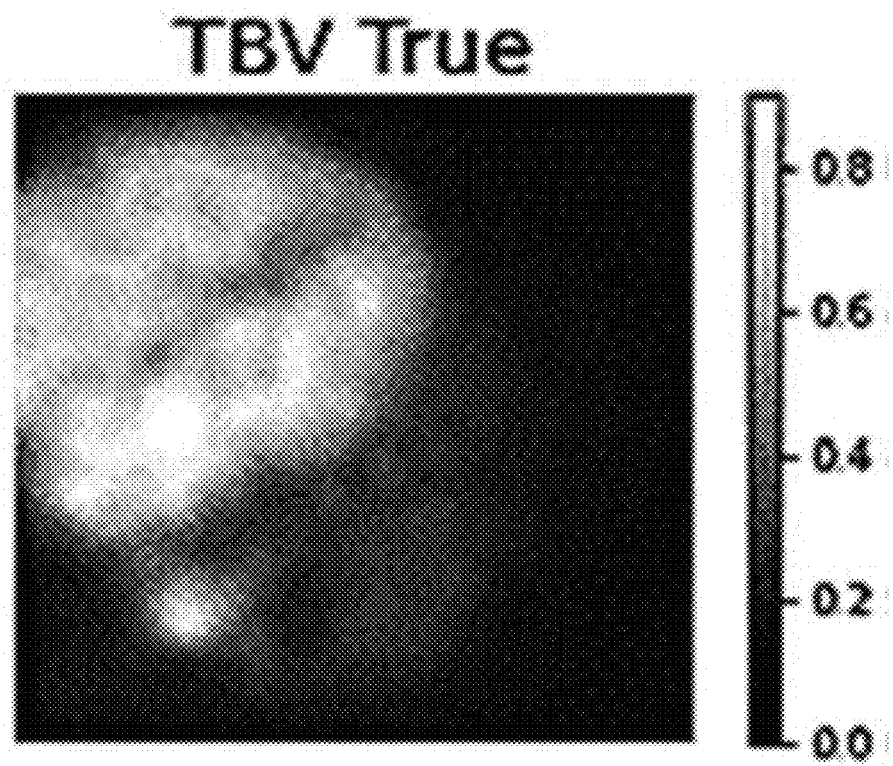
Figure 9:
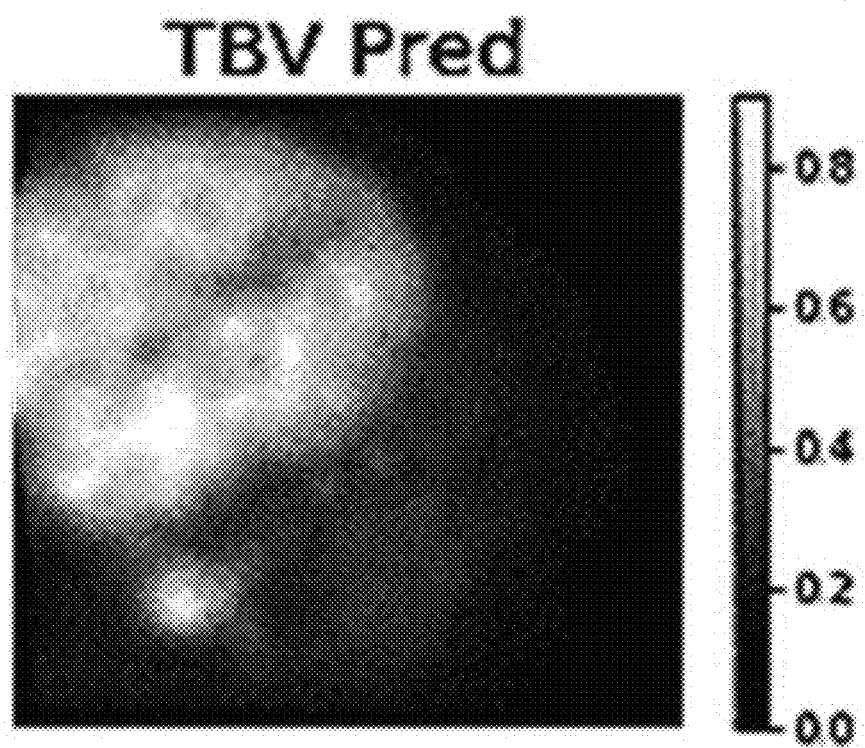
Figure 10:
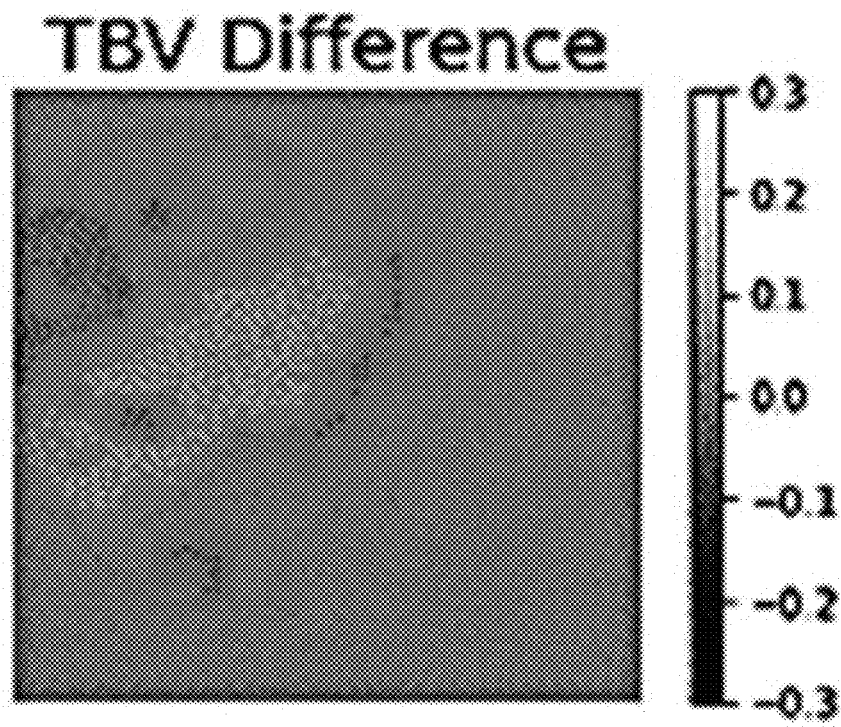
Figure 11:
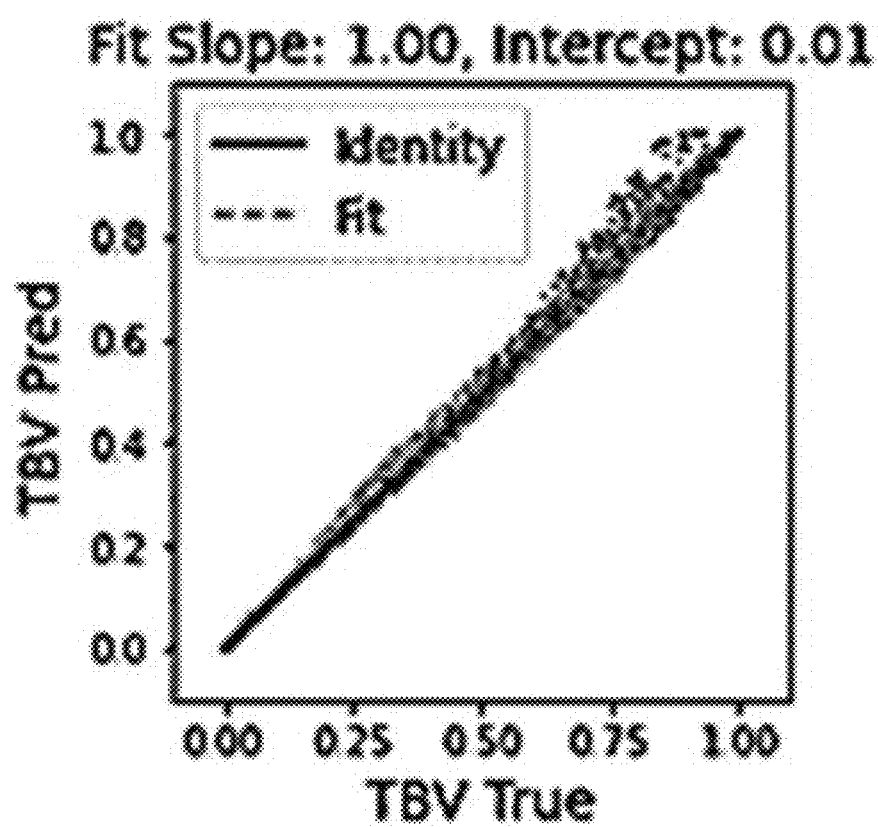
Figure 12:
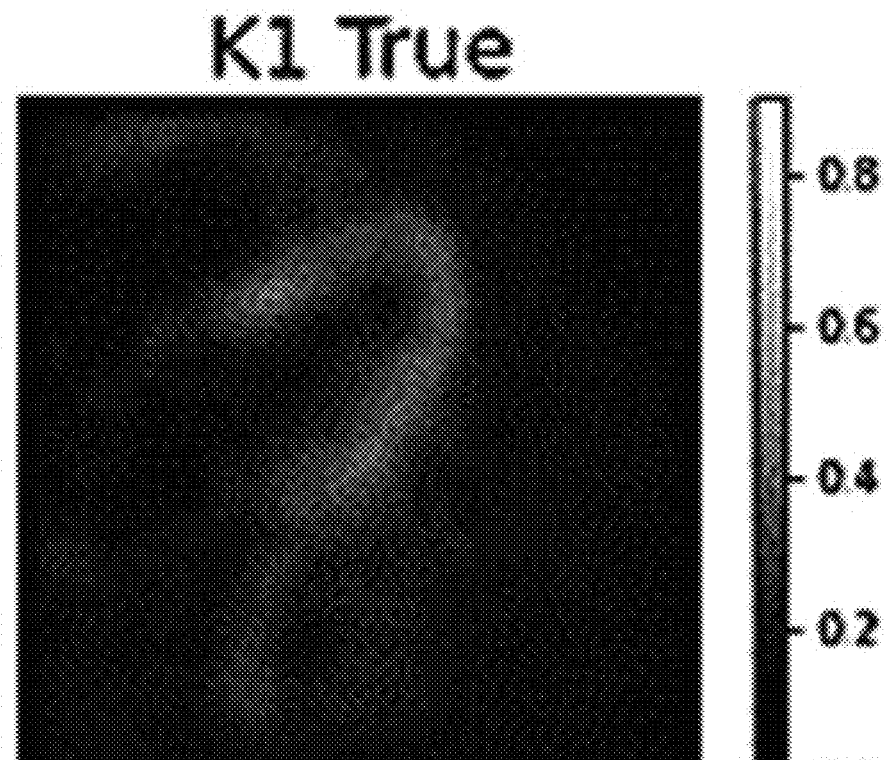
Figure 13:
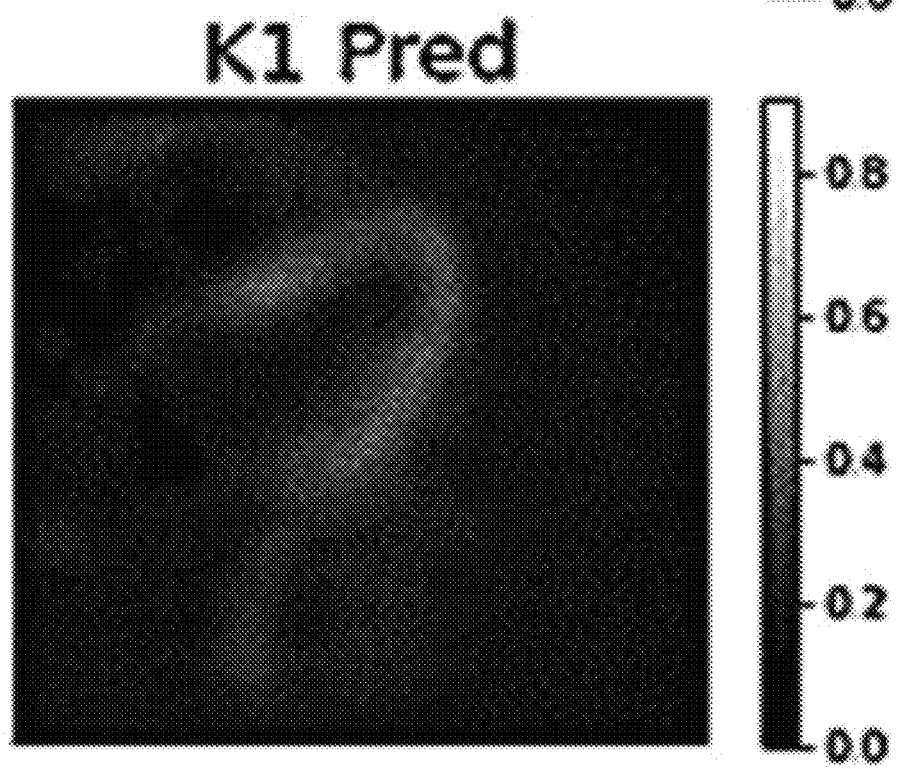
Figure 14:
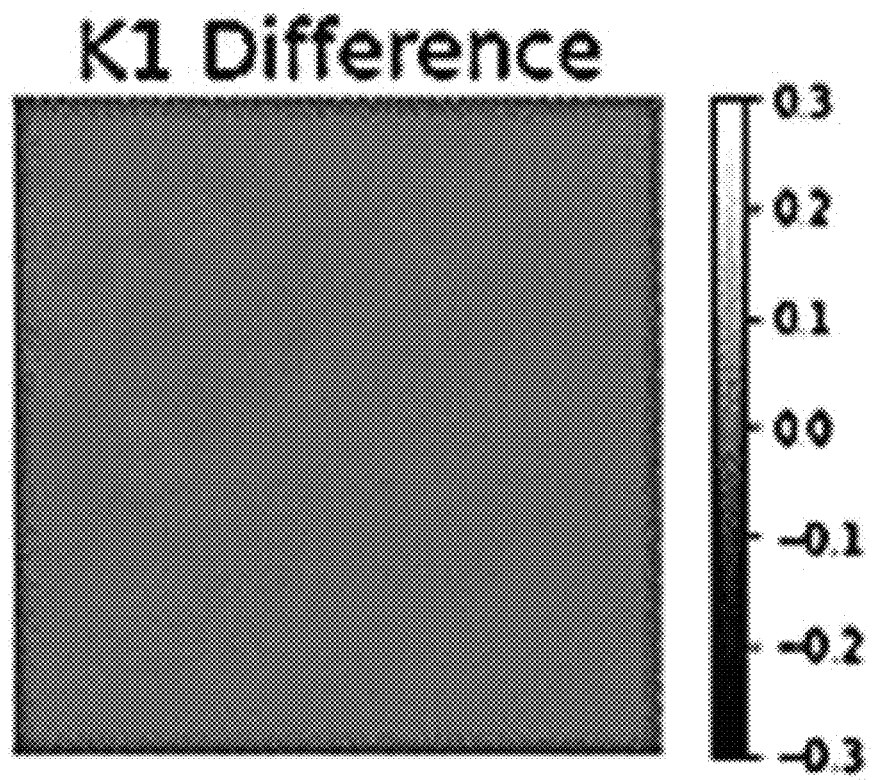
Figure 15:
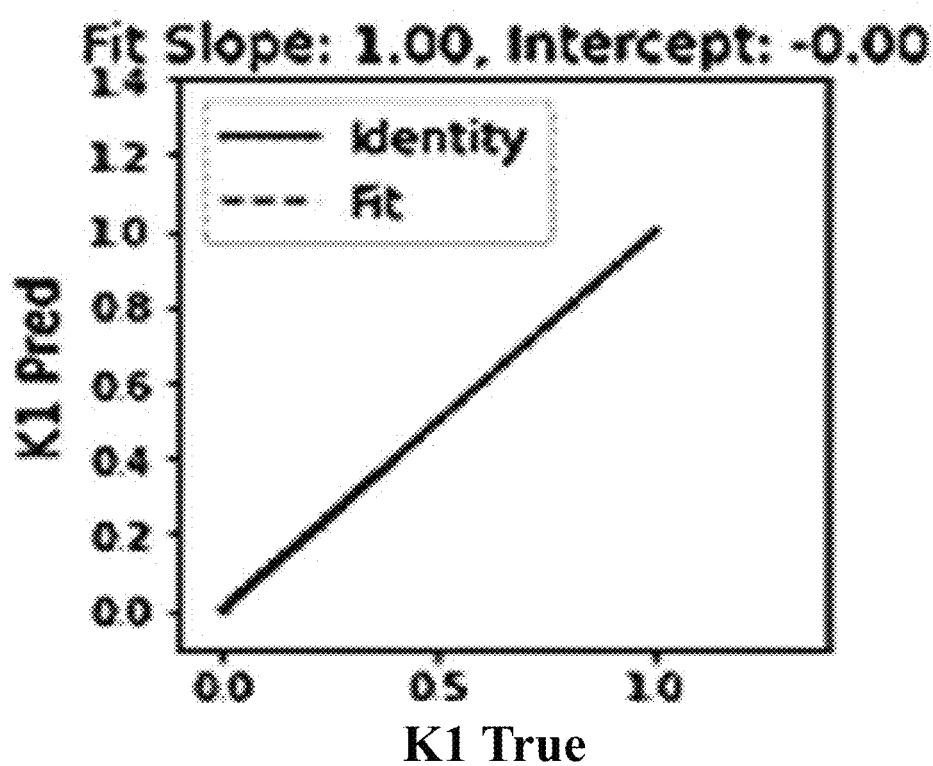
Figure 16:
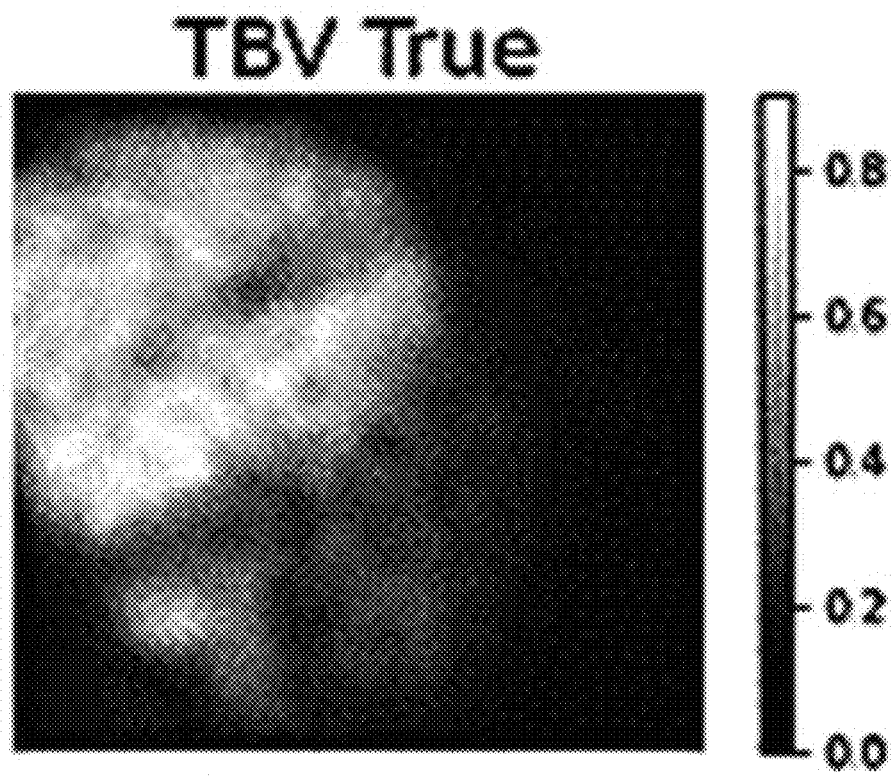
Figure 17:
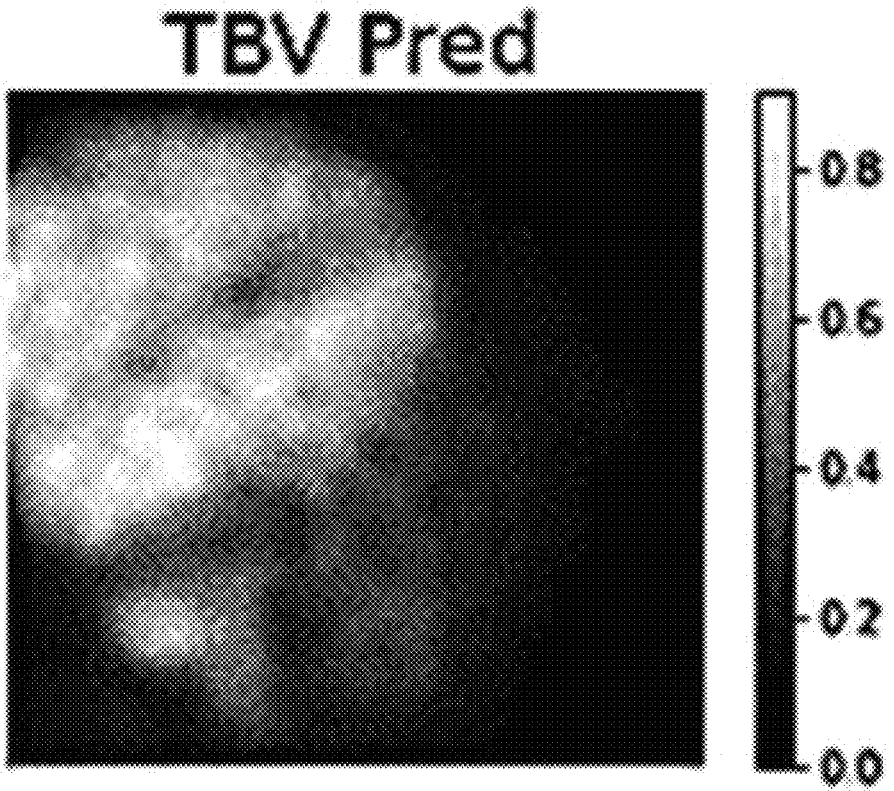
Figure 18:
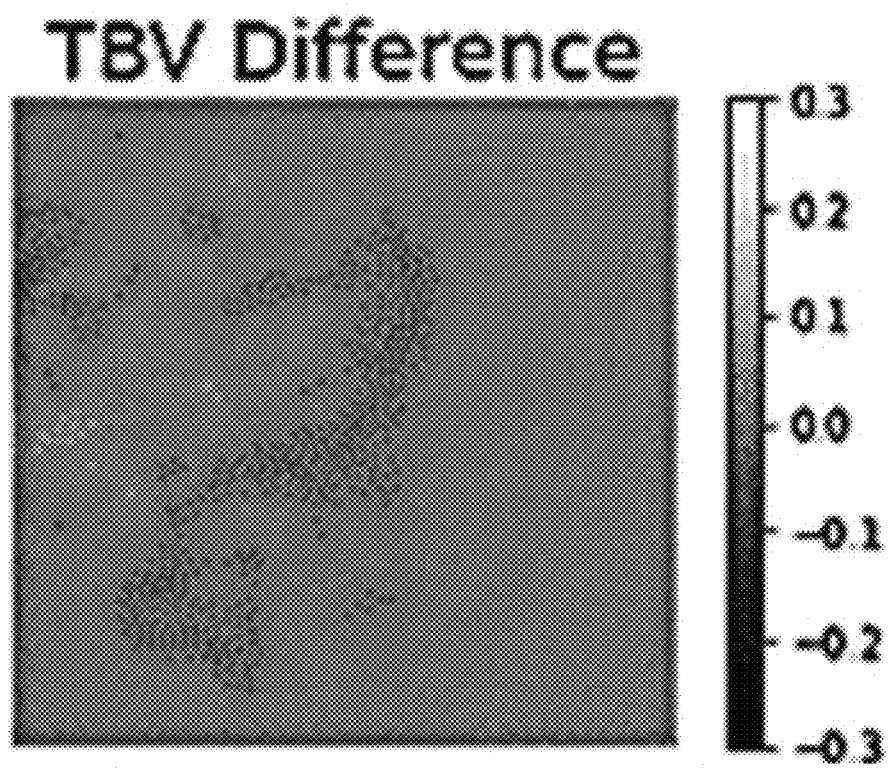
Figure 19:
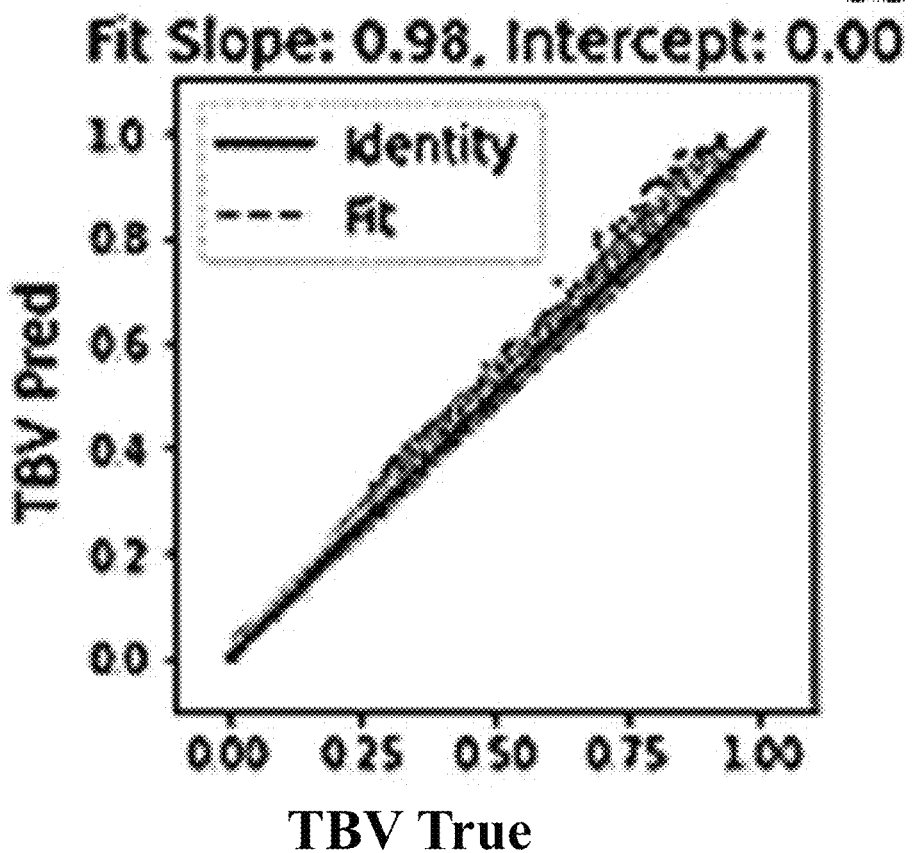

FIGS. 4-19 represent the ground truth vs AI-generated parametric maps. FIGS. 4-11 report the results for a patient's 82Rb Stress scan. Ground Truth $K_1$ parametric maps from nonlinear least squares method is depicted as $K_1$ True (shown in FIG. 4), the predicted $K_1$ map from the AI model is depicted as $K_1$ Predicted ($K_1$ pred.) (shown in FIG. 5), the difference between $K_1$ True and $K_1$ Pred. is depicted as $K_1$ difference ($K_1$ diff.) (shown in FIG. 6), and a correlation between the whole image $K_1$ True vs $K_1$ Pred. images (shown in FIG. 7). In FIG. 7 the solid line is the identity line and the dotted line is the fit of the correlation. FIGS. 12-19 report the results for a patient's 82Rb rest scan. Ground Truth $K_1$ parametric maps from nonlinear least squares method ($K_1$ True) (shown in FIG. 12), the predicted $K_1$ map from the AI model ($K_1$ Pred.) (shown in FIG. 13), the difference between $K_1$ True and $K_1$ Pred. ($K_1$ difference) (shown in FIG. 14), and a correlation between the whole image $K_1$ True vs $K_1$ Pred. images (shown in FIG. 15). In FIG. 15 the solid line is the identity line and the dotted line is the fit of the correlation.

In an embodiment of the present invention includes the image processing method to assess quantitative myocardial blood flow and myocardial flow reserve, wherein consistent image quality is observed in the dose range of Rb-82 is about 1 MBq to about 10,000 MBq.

In an embodiment of the present invention includes the image processing method to assess quantitative myocardial blood flow and myocardial flow reserve, wherein the imaging comprises X-ray radiography, Fluoroscopy, Magnetic resonance imaging (MRI), Computed Tomography (CT), Medical Ultrasonography or Ultrasound Endoscopy Elastography, Tactile imaging, Thermography Medical photography, and nuclear medicine functional imaging techniques e.g. positron emission tomography (PET), dynamic positron emission tomography, single-photon emission computed tomography (SPECT) imaging and/or combinations thereof.

In another embodiment of the present invention includes the image processing method to assess quantitative myocardial blood flow and myocardial flow reserve, wherein the dose of the imaging agent to be administered is calculated by automated generation and infusion system.

Yet in another embodiment of the present invention includes the image processing method to assess quantitative myocardial blood flow and myocardial flow reserve, wherein the input signal is enters multi-layer perceptron (MLP), artificial neural network (ANN), convolutional neural network and/or Long Short Term Memory (LSTM) network to simultaneously predict uptake rate ($K_1$), washout rate ($k_2$) and total blood volume (TBV), and wherein performing an assessment of the obtained images to diagnose disease state using deep neural network, artificial neural network, deep machine learning or combinations thereof.

In an embodiment of the present invention includes the image processing method to assess quantitative myocardial blood flow and myocardial flow reserve, wherein administering and performing the test, the steps comprising:
 a) generating a sufficient amount of Rb-82 by automated elution system of Sr-82/Rb-82 radionuclide generator;
 b) administering the generated dose of Rb-82 to the patient;
 c) performing a suitable imaging procedure to obtain better quality images of small regions; and
 d) performing an assessment of the obtained images to diagnose disease state using deep neural network, artificial neural network, deep machine learning, convolutional neural network, recurrent neural network, long short-term memory recurrent neural network (LSTM-RNN), generative adversarial networks (GANs), gated recurrent unit (GRU) network and/or combinations thereof.

In an embodiment of the present invention includes the image processing method to assess quantitative myocardial blood flow and myocardial flow reserve, wherein the method may further comprises administering a stress agent to the subject.

In another embodiment of the present invention includes the image processing method to assess quantitative myocardial blood flow and myocardial flow reserve, wherein the stress can be induced by administering a stress agent selected from adenosine, adenosine triphosphate, regadenoson, dobutamine, dipyridamole or exercise.

Yet in an embodiment of the present invention includes the image processing method to assess quantitative myocardial blood flow and myocardial flow reserve, wherein the subject weight ranges from 1 kg to 300 kg, preferably in the range of 20 kg to 200 kg.

In an embodiment of the present invention includes the image processing method to assess quantitative myocardial blood flow and myocardial flow reserve, wherein the automatic dose calculation further comprises other parameters selected from, type of radioisotope, radioisotope half-life, generator life (activity remaining in the radioisotope generator), generator yield, infusion time, flow rate, time lapse from generation to infusion of radioisotope, scanning instrument detector sensitivity, scanner resolution, type of camera or scanner, acquisition time, camera sensitivity, type of disease to be diagnosed, subject conditions like known allergies, heart function, liver function or kidney function or any other special need, subject's supplementary diseases, medications, type of imaging technique to be utilized like PET, SPECT, CT, MRI, and/or combinations thereof.

In another embodiment of the present invention includes the image processing method to assess quantitative myocardial blood flow and myocardial flow reserve, wherein the automated generation and infusion system comprises a cabinet, radioisotope generator, dose calibrator, computer, controller, display device, activity detector, cabinet, cart, waste bottle, sensors, shielding assembly, alarms or alerts mechanism, tubing, source vial, diluent or eluant, valves or combinations thereof. The automated generation and infusion system generates a radionuclide from a generator/column placed inside the system. A radionuclide eluate is generated from the generator by eluting the generator with suitable eluant like saline, which is then administered by the system automatically after activity measurements. The dose is calculated automatically by the system based on the entered subject parameters. The system is equipped to calculate the flow rate and infusion time depending on the dose to be administered. The automated generation and infusion system can comprise any radionuclide generator, which is suitable for administration to a subject like $^{82}Sr/^{12}Rb$ generator.

In an embodiment of the present invention includes the image processing method to assess quantitative myocardial blood flow and myocardial flow reserve, wherein the automated generation and infusion system is coupled to the imaging system electronically or communicatively. The coupled imaging system can provide alerts in case image quality is not up to the mark and require repeated administration or scanning.

In another embodiment of the present invention includes the image processing method to assess quantitative myocardial blood flow and myocardial flow reserve, wherein the automated generation and infusion system is embodied in a portable (or mobile) cart that houses some or all of the generator, the processor, the pump, the memory, the patient line, the bypass line, the positron detector, and/or the calibrator, sensors, dose calibrator, activity detector, waste bottle, controller, display, computer. The cart carrying the components for radioisotope generation and infusion is mobile and can be transferred from one place to another to the patient location or centers, hospitals as required.

Yet in an embodiment of the present invention includes the image processing method to assess quantitative myocardial blood flow and myocardial flow reserve, wherein the method of diagnosing/imaging blood perfusion or flow in the region of interest comprising: input subject parameters into the radioisotope generation and infusion system; automatically calculating the appropriate dose; generating a radionuclide from automated generation or infusion system based on required dose to be administered; administering the radionuclide to the subject in need thereof; performing PET or SPECT scanning of the region of interest; automated analysis of the images by computerized software; quantitative assessment of the blood flow in the region of interest; generating automated report of the assessment; providing appropriate therapy options for the subject.

In another embodiment of the present invention includes the image processing method to assess quantitative myocardial blood flow and myocardial flow reserve, wherein the subject is a human subject. The human subject is a male or female subject. The age of the subject may vary from 1 month to 120 years. The human subject includes neonates, pediatric, adults and/or geriatric population.

In another embodiment of the present invention includes the image processing method to assess quantitative myocardial blood flow and myocardial flow reserve, wherein all numbers disclosed herein can vary by 1%, 2%, 5%, 10%, or up to 20% if the word "about" is used in connection therewith. This variation may be applied to all numbers disclosed herein.

In another embodiment of the present invention includes the image processing method to assess quantitative myocardial blood flow and myocardial flow reserve, wherein 3D parametric images of MBF generated by present invention has better image quality and pixel. This invention also provides the recommendation alert to the medical staff regarding the detection of the coronary diseases by analyzing the generated 3D parametric images of MBF and/or MFR.

In another embodiment of the present invention includes the image processing method to assess quantitative myocardial blood flow and/or myocardial flow reserve, wherein 3D parametric images of MBF generated by present invention also recommend the calcium scoring. The coronary artery calcium (CAC) score reflects the total area of calcium deposits and the density of the calcium. A score of zero means no calcium is seen in the heart. It suggests a low chance of developing a heart attack in the future. When calcium is present, the higher the score, the higher the risk of heart disease. To evaluate the accuracy and reproducibility of visual estimation of coronary artery calcium (CAC) positron emission tomography (PET), dynamic positron emission tomography (PET), hybrid positron emission tomography (PET), computed tomography (CT) and single-photon emission computed tomography (SPECT)/CT myocardial perfusion imaging (MPI) scans are performed.

In another embodiment of the present invention includes the image processing method to assess quantitative myocardial blood flow and/or myocardial flow reserve, wherein the image reconstruction algorithms have been developed to improve the quality of images and using the AI algorithm to enhance the image reconstruction quality, which intended to do the image processing faster and reduce the doses of nuclear medicine up to 10 times during the myocardial perfusion imaging (MPI).

In another embodiment of the present invention includes the image processing method for AI models to generate blood flow parametric maps with high accuracy and in a timeframe acceptable for clinical use, which may enable future clinical implementation.

Each embodiment disclosed herein is contemplated as being applicable to each of the other disclosed embodiments. Thus, all combinations of the various elements described herein are within the scope of the invention.

This invention will be better understood by reference to the experimental data, which follow, but those skilled in the art will readily appreciate that the specific experiments detailed are only illustrative of the invention as described more fully in the claims, which follow thereafter.

EXPERIMENTAL METHOD

Example 1

Rb-82 is administered to patients. 20 subjects/patients (N=20) scans are selected with a wide range of uptake defect severities on Rb-82 stress PET perfusion imaging. The input signal is multi-layer perceptron (MLP), artificial neural network (ANN), convolutional neural network (CNN), recurrent neural network (RNN), long short-term memory recurrent neural network (LSTM-RNN), gated recurrent unit (GRU) network, Generative adversarial networks (GANs), deep machine learning and/or combinations thereof network to simultaneously predict uptake rate ($K_1$), $k_2$ and total blood volume (TBV) and the 3D parametric images of $K_1$, $k_2$ and TBV are combined to estimate the MBF and/or MFR.

Example 2

Rb-82 is administered to 40 patients (N=40) from two scanners (20 from GE Discovery 690, 20 from GE Discovery 600) were identified from Cardiac PET studies from 2019 covering a wide range of defect severities on 82Rb stress PET. Data from the Discovery 690 was split into training/validation/test sets with a 60:20:20 split. All Discovery 600 data constituted a separate hold-out test set. Image-derived arterial blood input functions (AIF) and voxel time series/time activity curves (TACs) in a 196×196× 98 mm$^3$ region around the heart were used for this study. Kinetic modeling is performed with one tissue compartment model (1TCM) with the classical nonlinear least squares (NLS) method to produce reference parametric maps. AIFs and voxel TACs were fed to a Convolutional/Long-Short Term Memory Neural Network (CNN-LSTM) to predict $K_1$ and TBV and the associated predicted TACs. The AI model was optimized to minimize the mean squared error between the input and predicted TACs (FIG. 3). The results are depicted below:

RESULTS

The AI model yielded accurate predictions of $K_1$ and TBV with average $R^2$ values of 0.998 and 0.991 for the Discovery 690 and 0.995 and 0.997 for the Discovery 600 hold-out test sets (reported in FIGS. 4-19). Generating parametric maps on a typical central processing unit (CPU) took an average 89.1 minutes for the classical NLS method and 7.21 seconds with AI enabled model as described in example 2, which is 741 times faster.

These two working examples of the present invention for AI models can generate blood flow parametric maps with high accuracy and in a timeframe acceptable for clinical use and thus may enable future clinical implementation.

What is claimed:

1. An image processing method to assess quantitative myocardial blood flow and/or myocardial flow reserve, comprising the steps of:
   a. pre-processing of images comprises:
      (i) reconstructing dynamic cine 3D tomographic myocardial perfusion imaging (MPI) data,
      (ii) isolating value at voxel (i,j,k) for each time point $t_i$ where i is from 1 to N,
      (iii) optionally, denoising to improve the quality of image,
      (iv) extracting blood input function from a region of interest (ROI) of the left ventricle blood cavity or other arterial blood region of interest (ROI),
      (v) estimating the distribution volume (DV), given by the ratio of uptake and washout rates ($K_1/k_2$), to stabilize and improve estimation of $K_1$, $k_2$ and total blood volume (TBV) and subsequent myocardial blood flow measures, and
      (vi) data normalization by dividing by the maximum of the blood input function;
   b. assessing the individual signals pre-processed in step (a) in order to generate $K_1$ and TBV parametric maps using artificial neural network;
   c. post-processing of $K_1$, $k_2$ and TBV parametric maps; and of rest and stress myocardial blood flow to estimate myocardial flow reserve (MFR) map and/or coronary flow reserve (CFR) map.

2. The image processing method to assess quantitative myocardial blood flow and myocardial flow reserve according to claim 1, wherein the image reconstruction of arrays is a dynamic series comprising the 3D tomographic volumes from PET reconstruction for the number of time steps, $t_i$ where i is from 1 to N.

3. The image processing method to assess quantitative myocardial blood flow and myocardial flow reserve according to claim 1, wherein a region of interest (ROI) can be manual and/or automatic procedures.

4. The image processing method to assess quantitative myocardial blood flow and myocardial flow reserve according to claim 1, wherein the data normalization by dividing by the maximum of the blood input function.

5. The image processing method to assess quantitative myocardial blood flow and myocardial flow reserve according to claim 1, wherein the data normalization for blood input function with the value is from 0 to 1.

6. The image processing method to assess quantitative myocardial blood flow and myocardial flow reserve according to claim 1, wherein the input signal is multi-layer perceptron (MLP) and/or artificial neural network (ANN) and/or convolutional neural network and/or long short term memory (LSTM) network to simultaneously predict uptake rate ($K_1$), $k_2$ and total blood volume (TBV).

7. The image processing method to assess quantitative myocardial blood flow and myocardial flow reserve according to claim 6, wherein the images produced regional flow and reserve values to highlight small regional flow defects.

8. The image processing method to assess quantitative myocardial blood flow and myocardial flow reserve according to claim 1, wherein the artificial neural networks are selected from the group consisting of multi-layer perceptron (MLP), artificial neural network (ANN), convolutional neural network (CNN), recurrent neural network (RNN), long short-term memory recurrent neural network (LSTM-RNN), gated recurrent unit (GRU) network, Generative adversarial networks (GANs), deep machine learning and/or combinations thereof.

9. The image processing method to assess quantitative myocardial blood flow and myocardial flow reserve according to claim 1, wherein to estimate distribution volume (DV) artificial neural network enter in multiple layers and wherein the multiple layers can be selected from the group consisting of the initial layer of the network, at an intermediate layer, at the penultimate layer, or combinations thereof.

10. The image processing method to assess quantitative myocardial blood flow and myocardial flow reserve according to claim 9, wherein the model predicts a $k_2$ (washout rate) value.

11. The image processing method to assess quantitative myocardial blood flow and myocardial flow reserve according to claim 1, wherein estimating $K_1$, $k_2$ and total blood volume (TBV) by performing on a voxel-wise basis using 1D signal CNN-LSTM to produce more accurate myocardial blood flow (MBF) estimations.

12. The image processing method to assess quantitative myocardial blood flow and myocardial flow reserve according to claim 1, wherein the images are characterized by administering Rb-82, O-15, N-13, Cu-62-PTSM, 99m-Tc-Sestamibi, Tl-201, and/or combinations thereof.

13. The image processing method to assess quantitative myocardial blood flow and myocardial flow reserve according to claim 1, wherein the images are characterized by administering Rb-82 in rest and stress PET perfusion imaging to highlights small regional flow defects.

14. The image processing method to assess quantitative myocardial blood flow and myocardial flow reserve according to claim 1, wherein the imaging agent or radionuclide is administered by automated generation and infusion system and/or intravenous administration of radiopharmaceuticals produced by fission, neutron activation, cyclotron and/or generator.

15. The image processing method to assess quantitative myocardial blood flow and myocardial flow reserve according to claim 1, wherein automated radioisotope generation and infusion system comprises Rb-82 elution system.

16. The image processing method to assess quantitative myocardial blood flow and myocardial flow reserve according to claim 1, wherein the images obtained fit to one-tissue-compartment model by predicting the value of the ratio of myocardial blood flow stress and myocardial blood flow rest to determine myocardial flow reserve and/or coronary flow reserve and wherein performing an assessment of the obtained images to diagnose disease state using multi-layer perceptron (MLP), artificial neural network (ANN), convolutional neural network (CNN), recurrent neural network (RNN), long short-term memory recurrent neural network (LSTM-RNN), gated recurrent unit (GRU) network, Generative adversarial networks (GANs), deep machine learning and/or combinations thereof.

17. The image processing method to assess quantitative myocardial blood flow and myocardial flow reserve according to claim 1, wherein the imaging comprises positron emission tomography (PET) imaging, dynamic positron emission tomography, single-photon emission computerized tomography (SPECT), magnetic resonance imaging (MRI), computed tomography (CT), and/or combinations thereof.

18. A myocardial image processing method to assess quantitative myocardial blood flow and myocardial flow reserve, comprising the steps of:
   a. pre-processing of images obtained by using Rubidium-82 radiotracer, comprising the step of:
      (i) reconstructing dynamic cine 3D tomographic myocardial perfusion imaging (MPI) data,
      (ii) isolating value at voxel (i,j,k) for each time point $t_i$ where i is from 1 to N,
      (iii) optionally, denoising to improve the quality of images,
      (iv) extracting blood input function from a region of interest (ROI) of the left ventricle blood cavity or other arterial blood region of interest (ROI),
      (v) estimating the distribution volume (DV), given by the ratio of uptake and washout rates ($K_1/k_2$) to stabilize and improve estimation of $K_1$, $k_2$ and total blood volume (TBV) and subsequent myocardial blood flow measures,
      (vi) data normalization by dividing by the maximum of the blood input function;
   b. applying the time series at voxel (i,j,k) and blood input function to artificial intelligence network simultaneously to predict uptake $K_1$, $k_2$ and TBV,
   c. post-processing of $K_1$, $k_2$ and TBV parametric maps comprises:
      (i) partial volume correction,
      (ii) extraction fraction to estimate myocardial blood flow (MBF) at rest and stress; and
   d. post-processing of rest and stress myocardial blood flow to estimate myocardial flow reserve (MFR) map and/or coronary flow reserve (CFR) map;
   wherein by analyzing the MBF and/or MFR map, recommending coronary diseases.

19. An image processing method to assess quantitative myocardial blood flow and myocardial flow reserve, comprising the steps of:
   a. pre-processing of images comprises:
      (i) reconstructing dynamic cine 3D tomographic myocardial perfusion imaging (MPI) data,
      (ii) isolating value at voxel (i,j,k) for each time point $t_i$ where i is from 1 to N,
      (iii) optionally, denoising to improve the quality of image,
      (iv) extracting blood input function from a region of interest (ROI) of the left ventricle blood cavity or other arterial blood region of interest (ROI),
      (v) estimating the distribution volume (DV), given by the ratio of uptake and washout rates ($K_1/k_2$) to stabilize and improve estimation of $K_1$, $k_2$ and total blood volume (TBV) and subsequent myocardial blood flow measures, and
      (vi) data normalization by dividing by the maximum of the blood input function;
   b. applying the time series at voxel (i,j,k) and blood input function to artificial intelligence network simultaneously to predict uptake $K_1$ and TBV, wherein the average $R^2$ values are in between 0.9 to 1:
   c. post-processing of $K_1$ and TBV parametric maps comprises:
      (i) partial volume correction,
      (ii) extraction fraction to estimate myocardial blood flow (MBF) at rest and stress; and
   d. post-processing of rest and stress myocardial blood flow to estimate myocardial flow reserve (MFR) map and/or coronary flow reserve (CFR) map;
   wherein the artificial neural networks are selected from the group consisting of, multi-layer perceptron (MLP), artificial neural network (ANN), convolutional neural network (CNN) and/or 1D convolutional neural network (1D-CNN), recurrent neural network (RNN), long short-term memory recurrent neural network (LSTM-RNN), gated recurrent unit (GRU) network, generative adversarial networks (GANs), deep machine learning and/or combinations thereof.

* * * * *